United States Patent
Rees et al.

(10) Patent No.: US 7,556,948 B2
(45) Date of Patent: Jul. 7, 2009

(54) METHOD FOR PRODUCING CRYSTALLIZED PLEUROMUTILINS

(75) Inventors: Michael John Rees, Harlow (GB); Keith Graham Robins, Worthing (GB); Anna Louisa Stefanska, Harlow (GB); Jan Edward Thirkettle, Brentford (GB); Michael Sidney Verrall, East Grinstead (GB); David Alan Yeandle, Worthing (GB)

(73) Assignee: Glaxo Group Limited, Greenford, Middlesex (GB)

( * ) Notice: Subject to any disclaimer, the term of this patent is extended or adjusted under 35 U.S.C. 154(b) by 363 days.

(21) Appl. No.: 10/524,099

(22) PCT Filed: Aug. 7, 2003

(86) PCT No.: PCT/GB03/03452

§ 371 (c)(1),
(2), (4) Date: Oct. 7, 2005

(87) PCT Pub. No.: WO2004/015122

PCT Pub. Date: Feb. 19, 2004

(65) Prior Publication Data

US 2006/0166341 A1    Jul. 27, 2006

(30) Foreign Application Priority Data

Aug. 9, 2002    (GB) ................. 0218578.3

(51) Int. Cl.
*A23K 1/17*    (2006.01)
*C12P 19/44*    (2006.01)

(52) U.S. Cl. ............... 435/117; 435/118; 435/119; 435/127; 435/77

(58) Field of Classification Search ............ None
See application file for complete search history.

(56) References Cited

U.S. PATENT DOCUMENTS

| | | | |
|---|---|---|---|
| 3,716,579 | A | 2/1973 | Knauseder et al. |
| 3,949,079 | A | 4/1976 | Brandl et al. |
| 4,089,891 | A | 5/1978 | Knauseder et al. |
| 4,092,424 | A | 5/1978 | Brandl et al. |
| 4,107,434 | A * | 8/1978 | Waldvogel ............ 544/59 |
| 4,129,721 | A | 12/1978 | Michel et al. |
| 4,130,709 | A | 12/1978 | Nagarajan |
| 4,247,542 | A | 1/1981 | Michel et al. |
| 4,308,375 | A | 12/1981 | Tang |
| 4,581,166 | A | 4/1986 | Peter et al. |
| 4,895,803 | A | 1/1990 | Hubner et al. |
| 5,545,654 | A | 8/1996 | Macher |
| 5,578,585 | A | 11/1996 | Matous et al. |
| 6,020,368 | A | 2/2000 | Hinks et al. |
| 6,121,281 | A | 9/2000 | Takle et al. |
| 6,281,226 | B1 | 8/2001 | Berry et al. |
| 6,878,704 | B2 | 4/2005 | Aitken et al. |
| 6,900,345 | B2 | 5/2005 | Elder et al. |
| 2003/0114674 | A1 | 6/2003 | Brooks et al. |
| 2005/0143393 | A1 | 6/2005 | Dean et al. |

FOREIGN PATENT DOCUMENTS

| | | |
|---|---|---|
| BE | 864361 | 8/1978 |
| CH | 572894 | 1/1976 |
| CH | 650 531 A | 7/1985 |
| CH | 650531 | 7/1985 |
| DE | 2809046 | 9/1979 |
| EP | 0707798 | 4/1996 |
| GB | 1197942 | 8/1967 |
| GB | 1200159 | 8/1967 |
| GB | 2025930 | 1/1980 |
| GB | 2121035 | 12/1983 |
| WO | WO 99/21855 | 5/1999 |
| WO | WO0027790 | 5/2000 |
| WO | WO0037074 | 6/2000 |
| WO | WO0073287 | 12/2000 |
| WO | WO 01 14310 | 3/2001 |
| WO | WO 01/74788 | 10/2001 |

OTHER PUBLICATIONS

Timothy Walford, et al; Poster presented at International Solvent Extraction Conference, Jul. 11-15, 1999; Barcelona.
Palma, N. et al., "Pleuromutilin Related Metabolites Produced by Submerged Culture of the Basidiomycetous Genus *Clitopilus* Kummer", (1984), Proceedings of European Congress Biotechnology, vol. *1*, pp. 533-542.
Kavanagh, Frederick, et al., (1951), Proc. Nat. Acad. Sci. USA, vol. *37*, pp. 570-574.
M. Anchel; Chemical Studies with Peuromutilin; J. Biol. Chem.; 1952; 133-139; 199.
Duilio Arigoni; La struttura di un terpene di nuovo genere; Gazz. Chim, Ital,; 1962; 884-901; 92.
H. Berner, et al.; Synthese AB-Trans-Anellierter derivate des Tricyclischen diterpens Pleuromutilin Durch Intramolekukaare I, 5-hydrid-Verschiebung; Tetrahedron; 1980; pp. 1807-1811; vol. 36.
H Berner, et al.; Chemie der Pleuromutiline, 10. Mitt.[1]: 1,2-Transposition der Carbonylfunktion im Cyclopentanonteil des tricyclischen Gerustes; Monatshefte fur Chemie; Chemical Monthly;1985; 1165-1176; 116.
A.J. Birch, et al.; The structure and some aspects of the biosynthesis of Pleuromutilin, Tetrahedron; 1966; pp. 359-387; Suppl. 8, Part II.
G. Brooks, et al; Pleuromutilins. Part 1; The identification of novel mutilin 14- carbamates; Bioorg. Med. Chem.; 2001; 1221-1231; vol. 9.

(Continued)

Primary Examiner—Irene Marx
(74) Attorney, Agent, or Firm—Linda E. Hall; Alan Scrivner; Charles M. Kinzig

(57) ABSTRACT

Invented are non-peptide TPO mimetics. Also invented is a method of treating thrombocytopenia, in a mammal, including a human, in need thereof which comprises administering to such mammal an effective amount of a selected hydroxy-1-azobenzene derivative.

19 Claims, No Drawings

OTHER PUBLICATIONS

H. Eger, et al.; New Pleuromutilins Derivatives with Enhanced Antimicrobial Activity, I. Synthesis; J. of Antibiotics; 1976; 915-922; vol. 29, No. 9.

H. Eger, et al.; New Pleuromutlin Derivatives with Enhanced Microbial Activity, II—Structure activity correlations; J. of Antibiotics; 1976; 923-927; vol. 29, No. 9.

G. Hogenauer; Antibiotics, ed F E Hahn; 1979; vol. V; part 1; p. 344; Springer-Verlag.

F. Kavanagh et al.; Proc. Nat. Acad. Sci.; 1951; 570-574; vol. 37; USA.

F. Kavanagh et al.; Antibiotic Substancs from Basidomycetes IX. Drosophila Subatrata; Proceedings of the National Academy of Sciences; Jul. 15, 1952; vol. 38, No. 7.

F. Knauseder, et al.;Pleuromutilins; Fermentation, Structure and Biosynthesis; J. of Antibiotics; 1976, 125-31; vol. 29, No. 2.

J.R. Markus; Method IV. Gas Chromatographic determination of tiamulin residues in swine liver; J. of AOAC International; 1993,; 451-458; vol. 76, No. 2.

J.R. Markus; Method V. Gas Chromatographic/Mass Spectrometric Confirmation of 8-hydroxymutilin, a tiamulin metabolite, in swin liver extracts; J. of AOAC Internationa; 1993; 459-60; vol. 76, No. 2.

N. Palma, et al.; Pleuromutilin related Metabolites produced by submerged culture of the Basidiomycetous Genus *Clitopilus* Kummer; Proceedings of European Congress Biotechnology; 1984; 533-542; vol. 1, 1984.

L.A. Paquette et al.; (+)—Pleuromutilin Synthetic Studies. Examples of Intramolecular Hydrogen Abstraction by the B-Carbon of a 2-cyclopentenone subunit with Resultant A- Coupling;J. Org. Chem.; 1988; 1461-1466; 53.

K. Riedl; Studies on Pleuromutilins and some of its derivatives; J. of Antibiotics; Feb. 1976; 132-139; vol. 29, No. 2.

H. Schneider, et al.; Process kinetic analysis of Pleuromutilins Fermentation; Part 1; Experiments; Bio process Engineering; 1987; 129-135; 2.

G. Schultz, et al.; Chemie der Pleuromutiline- VI, Vergleichende Untersuchung der 13C-NMR Spektren des tricyclischen diterpens mutilin und einer reihe von mutilinderivaten; Tetrahedron; 1984; 905-917; vol. 40, No. 5.

T. Walford, et al.; Poster presented at SCI Separation Science & Technology Group, Student Research Meeting; Jun. 10, 1998.

T. Walford, The Extraction of Microbial Metabolites from Fermentation Broths using Compressed Carbon Dioxide; Thesis submitted to the Facility of Engineering of the University of Birmingham for Degree of Doctor of Philosophy; Oct. 2000; pp. 1-223.

* cited by examiner

METHOD FOR PRODUCING CRYSTALLIZED PLEUROMUTILINS

This application is a 371 of International Application No. PCT/GB2003/003452, filed 7 Aug. 2003.

The present invention relates to a process for the preparation of one or more pleuromutilins, in particular pleuromutilin.

Pleuromutilin, the compound of formula (1), is a naturally occurring antibiotic which has antimycoplasmal activity and modest antibacterial activity. Mutilin and other compounds with a free OH at C-14 are inactive. The impact of further modification at C-14 on the activity of pleuromutilin has been investigated. It has been shown that the antimicrobial activity can be improved by replacing the glycolic ester moiety at position 14 by an R—X—CH$_2$CO$_2$— group, where R is an aliphatic or aromatic moiety and X is O, S, or NR' (H Egger and H Reinshagen, *J. Antibiotics*, 1976, 29, 923). Tiamulin, the compound of formula (2), which is used as a veterinary antibiotic, is a derivative of this type (G Hogenauer in Antibiotics, Vol. V, part 1, ed. F E Hahn, Springer-Verlag, 1979, p. 344).

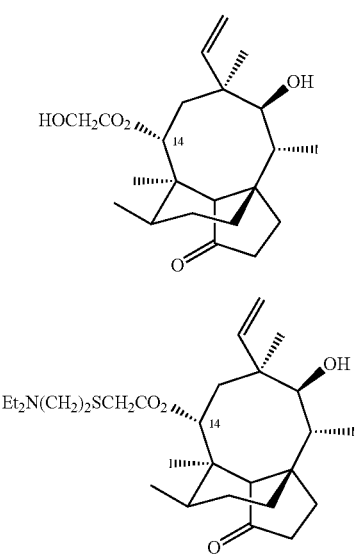

In this application, the non-conventional numbering system which is generally used in the literature (G Hogenauer, loc.cit.) is used.

More recently, further pleuromutilins have been described having the general formula (3).

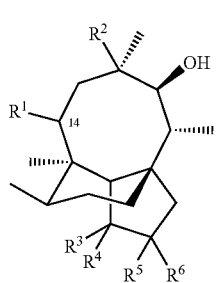

For example, WO 97/25309 (SmithKline Beecham) describes further modification of the acyloxy group, disclosing 14-O-carbamoyl derivatives in which the N-atom of the carbamoyl group is unsubstituted, mono- or di-substituted.

WO 98/05659 (SmithKline Beecham) discloses 14-O-carbamoyl derivatives in which the N-atom of the carbamoyl group is acylated by a group which includes an azabicyclic moiety.

WO 99/21855 (SmithKline Beecham) describes further derivatives in which the glycolic ester moiety at position 14 is replaced by the group R$^2$(CH$_2$)$_m$X(CH$_2$)$_n$CH$_2$COO— in which R$^2$ is a non-aromatic mono- or bicyclic group.

WO 00/27790 (SmithKline Beecham) describes C-14 spirocyclic, acylcarbamate, heteroaryalkyl carboxylate or arylalkoxyalkyl carboxylate derivatives.

WO 00/37074 (SmithKline Beecham) describes further derivatives having a heteroaryl acetate substituent at the C-14 position.

WO 00/73287 (SmithKline Beecham) describes further derivatives having an isoxazoline carboxylate substituent at the C-14 position.

WO 01/14310 (SmithKline Beecham) describes further derivatives having a β-ketoester substituent at the C-14 position.

WO 01/74788 (SmithKline Beecham) describes 2-hydroxymutilin carbamate derivatives.

WO 02/12199 (SmithKline Beecham) describes derivatives having a heterocyclic ester substituent at the C-14 position.

WO 02/30929 (SmithKline Beecham) describes derivatives having an oxycarbonyl carbamate substituent at the C-14 position.

WO 02/38528 (SmithKline Beecham) describes derivatives having a malonamide or malonic ester substituent at the C-14 position.

In addition, 19,20-dihydro-2α-hydroxy-mutilin is described by G. Schulz and H. Berner in *Tetrahedron*, 1984, vol. 40, pp 905-917, and a number of C-14 ether, carbamate, amide and urea derivatives are described by Brooks et al. in Bioorg. Med. Chem, 2001, vol. 9, pp1221-1231.

Pleuromutilin may be produced by the fermentation of microorganisms such as *Clitopilus* species, *Octojuga* species and *Gerronema* species. These organisms may also produce a number of related pleuromutilins, for example mutilin 14-acetate. These other pleuromutilins are produced at varying levels depending on the organism and the culture conditions (F Knauseder and E Brandl, Pleuromutilins: Fermentation, Structure and Biosynthesis, *J. Antibiotics*, 1976, 29, 125-131), but they are typically less abundant than pleuromutilin.

Following fermentation, pleuromutilin and the other pleuromutilins are present in both the fermentation medium and within the microorganism cells. Known methods for the extraction and subsequent purification of pleuromutilins are disclosed in U.S. Pat. Nos. 4,092,424, 4,129,721, 4,247,542, GB patent 1,197,942 and published in papers such as Antibiotic Substances from Basidiomycetes VIII, F. Kavanagh et al., *Proc. N.A.S.*, 1951, 570-574. The methods include extraction of the filtered broth with a water immiscible solvent e.g. toluene, ethyl acetate or chloroform. Extractions of pleuromutilins from the culture mycelium with a water miscible solvent, for example acetone, followed by extraction with a water immiscible solvent, for example ethyl acetate, are also described. The pleuromutilins are subsequently crystallised from the organic solvent. The disadvantages of these methods is that they require the separation of the harvested fermentation broth into mycellial pellet and culture liquid for individual extraction.

Accordingly, there is a need to provide an improved method for the extraction of pleuromutilins, in particular pleuromutilin, following fermentation which provides an efficient extraction suited to large scale industrial operations.

The solution to this problem is provided by a process comprising extraction of the whole unfiltered culture medium or fermentation broth, i.e. both fermentation liquid and mycelium, with a water immiscible organic solvent with high specificity for extracting pleuromutilins.

This results in a product of high purity that can be crystallised directly without the need for intermediate purification steps. The benefits and improvements of this process thus include fewer processing steps with high yields as the pleuromutilins present in both the mycelium and the supernatant are recovered.

Thus according to the present invention there is provided a method for preparing one or more pleuromutilins comprising the steps of:

a) culturing a pleuromutilins-producing microorganism in a liquid culture medium; and b) extracting the pleuromutilins from the unfiltered culture medium with a water immiscible organic solvent.

The resulting pleuromutilins are preferably further purified, for example by crystallisation. Thus the present invention also provides a method for preparing one or more pleuromutilins comprising the steps of:

a) culturing a pleuromutilins-producing microorganism in a liquid culture medium;

b) extracting the pleuromutilins from the unfiltered culture medium with a water immiscible organic solvent;

c) concentrating the extracted pleuromutilins; and d) crystallizing the pleuromutilins.

Additionally, the extracted pleuromutilins may be decolorised prior to crystallisation using, for example, activated carbon. Decolorisation may be carried out either after the pleuromutilins have been extracted from the unfiltered culture medium (Step b) or after the extracted pleuromutilins have been concentrated (Step c). Preferably the decolonization is carried out after the extracted pleuromutilins have been concentrated (Step c).

The pleuromutilins-producing microorganism may be any microorganism capable of producing one or more pleuromutilins. Preferably, the pleuromutilins-producing microorganism used in the process of the present invention is a *Clitopilus* species, for instance *Clitopilus passeckerianus* NRRL 3100/DSM 1602, *Clitopilus passeckerianus* CBS 299.35, *Clitopilus passeckerianus* CBS 330.85, *Clitopilus pinsitus* CBS 623.70 or *Clitopilus hobsonii* CBS 270.36; an *Octojuga* species, for instance *Octojuga pseudopinsitus* NRRL11179; a *Gerronema* species, for instance *Gerronema josserandii* CBS 309.36; or a mutant of any such species. The pleuromutilins-producing microorganism may also be a *Psathyrella* species, for instance *Psathyrella subatrata* CBS 325.39, or a mutant of such species. Particularly preferred is a *Clitopilus* species or a mutant thereof, especially *Clitopilus passeckerianus* NRRL 3100 or a mutant thereof. Mutants can be prepared by conventional means, for example by UV or chemical mutagenesis.

The microorganisms can be grown by fermentation culture techniques well known to those skilled in the art such as those disclosed in U.S. Pat. No. 4,092,424.

In the process of the present invention, the water immiscible organic solvent is typically an aromatic hydrocarbon or a water immiscible aliphatic ketone. A preferred aromatic hydrocarbon is toluene and a preferred water immiscible aliphatic ketone is 4-methyl-2-pentanone (MIBK).

The extraction can be conducted at about 10° C. to about 50° C. Preferably, the extraction is conducted at about 20° C. The pH of the aqueous solution prior to extraction should be in the range 3 to 9. Preferably the pH is near neutrality, e.g. pH 6 to 8, more preferably pH 6.9±0.2. The pH of the medium may be adjusted by addition of a suitable acid or base, for example acetic acid or sodium hydroxide.

In general, ratio ranges of 4:1 to 1:4 equivalent volume of organic solvent to unfiltered culture medium can be used for the extraction. The preferred ratio is 1:2 organic solvent to unfiltered culture medium.

In one embodiment of the present invention, the solvent and unfiltered culture medium may be mixed inline by impinging the two streams and passing through a baffled tube or mechanical mixer. The phases may then be separated by passing through a centrifugal separator such as a disk stack centrifuge or preferably a combined extraction/separation decanter such as a scroll (counter current) decanter.

Alternatively, the extraction may be carried out by stirring the two phases in a tank and allowing the combined phases to settle under gravity or by using a counter current extraction column or similar device which provides intimate contact between the two phases and subsequent separation.

After separation of the organic layer, concentration of the extract by volume reduction of the solvent may be carried out in vacuo or by other methods well-known to those skilled in the art. After volume reduction, the pleuromutilins may be crystallised from the concentrated extract. The pleuromutilins can be directly crystallised from toluene or MIBK. Preferably MIBK crystallisations are carried out with the addition of miscible non-polar solvents, for example heptane.

The concentration of the toluene solution used for crystallisation may be from 10% to 50% w/w. The initial temperature of the toluene is preferably from 60° C. to 70° C., followed by cooling to from 0° C. to 5° C. for 8-10 hours to complete crystallisation.

The concentration of the MIBK solution used for crystallisation may be from 20% to 45% w/w, preferably from 35 to 40% w/w. The initial temperature of the MIBK is generally from 45° C. to 60° C., especially from 50 to 55° C., cooling to from 25° C. to 35° C., especially approximately 30° C., to initiate crystallisation. Up to about 2 volumes of heptane may be added to aid crystallisation. Preferably 1 to 1.5 volumes are added. The heptane may be added over 15 min to 1 hour. After heptane addition, the crystallisation mix is preferably cooled to 0-5° C. but may be held at ambient temperature.

As discussed above, prior to crystallisation, the pleuromutilins extract or concentrate may optionally be decolorised using activated carbon. For example, the mutilin concentrate may be batch treated with powdered or granulated charcoal, or passed through a cartridge, column or filter bed packed with charcoal. A ratio of up to 1:15 carbon:pleuromutilins w/w is normally used. The concentration of pleuromutilins in the MIBK for the decolourisation step may be 1-40%, preferably 7-20% w/w. In the case of batch treatment, an activated carbon such as Norit GSK (Norit UK Ltd, Clydesmill Place, G32 8RF, UK) may be used.

The crystallised product prepared according to the process of the present invention may comprise one or more pleuromutilins. Generally, the crystallised product is pleuromutilin which may contain minor related pleuromutilins in addition to pleuromutilin, in particular mutilin 14-acetate. The crystallised product may be used to prepare semi-synthetic pleuromutilins derivatives without further purification. For example, a mixture of pleuromutilin and mutilin 14-acetate can be hydrolysed to mutilin, which may then be used as a synthetic starting material. However, the process of the present invention is preferably used to produce pleuromutilin. Accordingly, the crystallised pleuromutilins product may be further purified by methods such as recrystallisation, for example recrystallisation from ethyl acetate and heptane or from MIBK and heptane.

In one embodiment of the present invention, mutilin 14-acetate may be selectively removed from the pleuromutilins product by recrystallisation from ethyl acetate and heptane. The concentration of pleuromutilins in ethyl acetate for crystallisation may be from 20 to 40% w/w, preferably from 20 to 30% w/w, especially about 30% w/w. The initial temperature for the process is preferably from 45° C. to 50° C., cooling to from 15° C. to 25° C., especially about 20° C., to initiate crystallisation, followed by heptane addition and further cooling to ambient, or preferably 0 to 5° C., 0 to 2 volumes of heptane, preferably 1-1.5 volumes, may be added to aid crystallisation. The heptane is typically added over a period of 15 min to 1 hour, but may be added more slowly.

In a further embodiment of the present invention, mutilin 14-acetate may be selectively removed from the pleuromutilins product by recrystallisation from MIBK and heptane. Where the initial extraction and crystallisation has been carried out using MIBK, use of MIBK in the recrystallisation step has the advantage that recrystallisation can be carried out on either dried product or in situ on wet cake (i.e. the pleuromutilins product obtained directly from crystallisation, prior to drying) without generating a complex mixture of solvents. The concentration of the MIBK solution used for recrystallisation may be from 20% to 45% w/w, preferably from 35 to 45% w/w. The initial temperature of the MIBK is generally from 45° C. to 65° C., especially about 60° C. Up to about 2 volumes of heptane may be added to aid crystallisation. Preferably 1 to 1.5 volumes are added. The heptane may be added over 10 min to 1 hour, preferably over 10 min to 30 min. After heptane addition, the crystallisation mix is preferably cooled to 0-5° C.

In one preferred embodiment, the pleuromutilins prepared according to the process of the present invention are used to prepare the semi-synthetic pleuromutilins derivatives described in WO 99/21855, which are incorporated herein by reference. Thus, the pleuromutilins prepared according to the process of the present invention are preferably used to prepare a semi-synthetic pleuromutilins derivative of general formula (4A) or (4B):

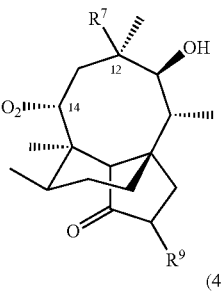

(4A)

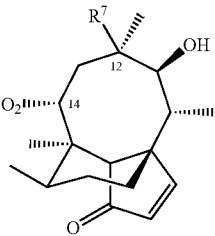

(4B)

in which:
each of n and m is independently 0, 1 or 2;
X is selected from —O—, —S—, —S(O)—, —SO$_2$—, —CO.O—, —NH—, —CONH—, —NHCONH— and a bond;
R$^7$ is vinyl or ethyl;

R$^8$ is an optionally substituted non-aromatic monocyclic or bicyclic group containing one or two basic nitrogen atoms and attached through a ring carbon atom;
R$^9$ is H or OH; or
the moiety R$^8$(CH$_2$)$_m$X(CH$_2$)$_n$CH$_2$COO at position 14 of (4A) or (4B) is replaced by R$^a$R$^b$C=CHCOO in which one of R$^a$ and R$^b$ is hydrogen and the other is R$^8$ or R$^a$ and R$^b$ together form R$^8$; or
a pharmaceutically acceptable salt thereof.

When R$^8$ is monocyclic, it typically contains from 4 to 8 ring atoms, and, when bicyclic, it typically contains from 5 to 10 ring atoms in each ring, and is optionally substituted by up to 3 substituents. Suitable substituents include alkyl, alkyloxy, alkenyl and alkenyloxy, each of which may be carried by either a bridgehead or a non-bridgehead carbon atom. In addition, the or each nitrogen atom may be substituted by oxygen, to form an N-oxide, or by mono- or dialkyl, in which case it will be appreciated that a quaternary cation can be formed. The counterion may be a halide ion such as chloride or bromide, preferably chloride. The aza ring system additionally may contain one or more double bonds.

Representative bicyclic and monocyclic groups for R$^8$ include piperidinyl, pyrrolidyl, quinuclidinyl, azabicyclo[2.2.1]heptyl, azabicyclo[4,3,0]nonyl, azabicyclo[3.2.1]octyl, azabicyclo[3,3,0]octyl, azabicyclo[2.2.2]octyl, azabicyclo[3.2.1]octenyl, azabicyclo[3.3.1]nonyl and azabicyclo[4.4.0]decyl, all of which may be substituted or unsubstituted. Preferred examples for R$^8$ include quinuclidinyl.

Preferably, n is 0. Preferably, m is 0 or 1.
Preferred compounds are those of formula (4A).
Alkyl and alkenyl groups referred to herein with reference to formula (4A) or (4B) include straight and branched groups containing up to six carbon atoms and are optionally substituted by one or more groups selected from the group consisting of aryl, heterocyclyl, (C$_{1-6}$)alkoxy, (C$_{1-6}$)alkylthio, aryl (C$_{1-6}$)alkoxy, aryl(C$_{1-6}$)alkylthio, amino, mono- or di-(C$_{1-6}$) alkylamino, cycloalkyl, cycloalkenyl, carboxy and esters thereof, amides of carboxy, ureido, carbamimidoyl (amidino), guanidino, alkyl-sulfonyl, amino-sulfonyl (C$_{1-6}$)acyloxy, (C$_{1-6}$)acylamino, azido, hydroxy, and halogen.

Cycloalkyl and cycloalkenyl groups referred to herein with reference to formula (4A) or (4B) include groups having from three to eight ring carbon atoms and are optionally substituted as described hereinabove for alkyl and alkenyl groups.

When used herein with reference to formula (4A) or (4B), the term "aryl" means single and fused rings suitably containing from 4 to 7, preferably 5 or 6, ring atoms in each ring, which rings may each be unsubstituted or substituted by, for example, up to three substituents. A fused ring system may include aliphatic rings and need include only one aromatic ring. Representative aryl groups include phenyl and naphthyl such as 1-naphthyl or 2-naphthyl.

Suitably any aryl group, including phenyl and naphthyl, may be optionally substituted by up to five, preferably up to three substituents. Suitable substituents include halogen, (C$_{1-6}$)alkyl, aryl, aryl(C$_{1-6}$)alkyl, (C$_{1-6}$)alkoxy, (C$_{1-6}$)alkoxy (C$_{1-6}$)alkyl, halo(C$_{1-6}$)alkyl, aryl(C$_{1-6}$)alkoxy, hydroxy, nitro, cyano, azido, amino, mono- and di-N-(C$_{1-6}$)alkylamino, acylamino, arylcarbonylamino, acyloxy, carboxy, carboxy salts, carboxy esters, carbamoyl, mono- and di-N-(C$_{1-6}$)alkylcarbamoyl, (C$_{1-6}$)alkoxycarbonyl, aryloxycarbonyl, ureido, guanidino, sulphonylamino, aminosulphonyl, (C$_{1-6}$)alkylthio, (C$_{1-6}$)alkyl sulphinyl, (C$_{1-6}$)alkylsulphonyl, heterocyclyl and heterocyclyl (C$_{1-6}$)alkyl. In addition, two adjacent ring carbon atoms may be linked by a (C$_{3-5}$)alkylene chain, to form a carbocyclic ring.

When used herein with reference to formula (4A) or (4B), the terms "heterocyclyl" and "heterocyclic" suitably include, unless otherwise defined, aromatic and non-aromatic, single and fused, rings suitably containing up to four heteroatoms in each ring, each of which is selected from oxygen, nitrogen and sulphur, which rings, may be unsubstituted or substituted by, for example, up to three substituents. Each heterocyclic ring suitably has from 4 to 7, preferably 5 or 6, ring atoms. A fused heterocyclic ring system may include carbocyclic rings and need include only one heterocyclic ring.

Preferably substituents for a heterocyclyl group are selected from halogen, $(C_{1-6})$alkyl, aryl$(C_{1-6})$alkyl, $(C_{1-6})$alkoxy, $(C_{1-6})$alkoxy$(C_{1-6})$alkyl, halo$(C_{1-6})$alkyl, hydroxy, amino, mono- and di-N-$(C_{1-6})$alkyl-amino, acylamino, carboxy, carboxy salts, carboxy esters, carbamoyl, mono- and di-N-$(C_{1-6})$alkylcarbonyl, aryloxycarbonyl, $(C_{1-6})$alkoxycarbonyl$(C_{1-6})$alkyl, aryl, oxy groups, ureido, guanidino, sulphonylamino, aminosulphonyl, $(C_{1-6})$alkylthio, $(C_{1-6})$alkylsulphinyl, $(C_{1-6})$alkylsulphonyl, heterocyclyl and heterocyclyl$(C_{1-6})$alkyl.

In a further preferred embodiment, the pleuromutilins prepared according to the process of the present invention are used to prepare the semi-synthetic pleuromutilins derivatives described in WO 01/74788, which are incorporated herein by reference. Thus, the pleuromutilins prepared according to the process of the present invention are preferably used to prepare a semi-synthetic pleuromutilins derivative of general formula (5):

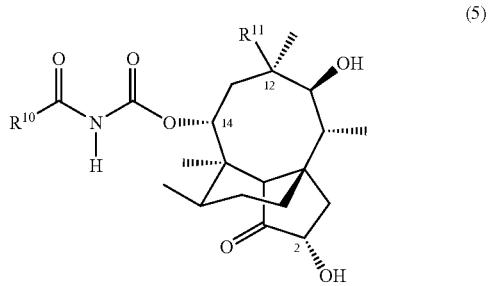

(5)

in which:
$R^{10}$ is a 5- or 6-membered optionally substituted heteroaryl group; and
$R^{11}$ is vinyl or ethyl;
or a pharmaceutically acceptable salt thereof.

Examples of heteroaryl groups for $R^{10}$ include those having a 5 or 6-membered single ring comprising 1 or 2 nitrogen atoms and optionally comprising a further heteroatom selected from oxygen or sulphur, for example pyridine, pyridazine, pyrimidine, pyrazine, isoxazole, thiazole, imidazole, pyrazole; or a 5 or 6-membered ring comprising 3 nitrogen atoms, for example, 1,2,3-triazole, 1,2,4-triazole; or a 5 or 6-membered ring comprising 1 or 2 nitrogen atoms fused to a benzene ring, for example, benzimidazole. Further examples of heteroaryl groups for $R^{10}$ include those having a 5 or 6-membered ring comprising 1 or 2 nitrogen atoms fused to a second 5 or 6-membered optionally substituted heteroaryl ring comprising 1 or 2 nitrogen atoms.

Representative examples of such heteroaryl groups for $R^{10}$ include, for example, pyridine, pyrazine, pyridazine, 3-oxo-3,4-dihydropyrido[2,3-b]pyrazine, pyrazolo[1,5-a]pyrimidine, pyrimidine, and thiazole. Preferred examples of such heteroaryl groups for $R^{10}$ include, for example, pyridine, pyrimidine, and thiazole.

Representative optional substituents for $R^{10}$ include amino, mono- or di-$(C_{1-6})$alkylamino, $(C_{1-6})$alkyl, $(C_{1-6})$alkoxy, nitro and N-containing heterocyclyl such as piperidinyl-4-yl which may be optionally substituted. Typically $R^{10}$ may comprise one or two substituents.

When used herein with reference to formula (5), the term "aryl" refers to, unless otherwise defined, phenyl or naphthyl. A substituted aryl group comprises up to five, preferably up to three substituents.

Suitable substituents for an aryl group, including phenyl when forming part of a benzyl group, include, for example, and unless otherwise defined, halogen, $(C_{1-6})$alkyl, aryl, aryl$(C_{1-6})$alkyl, $(C_{1-6})$alkoxy, $(C_{1-6})$alkoxy$(C_{1-6})$alkyl, halo$(C_{1-6})$alkyl, aryl$(C_{1-6})$alkoxy, hydroxy, nitro, cyano, azido, amino, mono- and di-N-$(C_{1-6})$alkylamino, acylamino, arylcarbonylamino, acyloxy, carboxy, carboxy salts, carboxy esters, carbamoyl, mono- and di-N-$(C_{1-6})$alkylcarbamoyl, $(C_{1-6})$alkoxycarbonyl, aryloxycarbonyl, ureido, guanidino, $(C_{1-6})$alkylguanidino, amidino, $(C_{1-6})$alkylamidino, sulphonylamino, aminosulphonyl, $(C_{1-6})$alkylthio, $(C_{1-6})$alkylsulphinyl, $(C_{1-6})$alkylsulphonyl, heterocyclyl, heteroaryl, heterocyclyl$(C_{1-6})$alkyl and heteroaryl$(C_{1-6})$alkyl. In addition, two adjacent ring carbon atoms may be linked by a $(C_{3-5})$ alkylene chain, to form a carbocyclic ring.

When used herein with reference to formula (5), the terms "alkyl" and "alkenyl" refer to (individually or as part of alkoxy or alkenyloxy) straight and branched groups containing up to six carbon atoms.

When used herein with reference to formula (5), the terms "cycloalkyl" and "cycloalkenyl" refer to groups having from three to eight ring carbon atoms.

When substituted, an alkyl, alkenyl, cycloalkyl or cycloalkenyl group may comprise up to four substituents, preferably up to two substituents. Suitable substituents for alkyl, alkenyl, cycloalkyl or cycloalkenyl groups include aryl, heteroaryl, heterocyclyl, $(C_{1-6})$alkoxy, $(C_{1-6})$alkylthio, aryl$(C_{1-6})$alkoxy, aryl$(C_{1-6})$alkylthio, amino, mono- or di-$(C_{1-6})$alkylamino, cycloalkyl, cycloalkenyl, carboxy and esters thereof, amide, ureido, guanidino, $(C_{1-6})$alkylguanidino, amidino, $(C_{1-6})$alkylamidino, $(C_{1-6})$acyloxy, azido, hydroxy, and halogen.

When used herein with reference to formula (5) the terms "heterocyclyl" and "heterocyclic" refer to, unless otherwise defined, non-aromatic, single and fused, rings suitably containing up to four heteroatoms in each ring, each of which is selected from oxygen, nitrogen and sulphur. Each heterocyclic ring preferably has from 4 to 7, preferably 5 or 6, ring atoms. A fused heterocyclic ring system may include carbocyclic rings and need include only one heterocyclic ring.

When substituted, a heterocyclyl group may comprise up to three substituents. Preferably a substituent for a heterocyclyl group is selected from oxo, and the group hereinbefore defined as suitable aryl substituents.

When used herein with reference to formula (5), the term "heteroaryl" suitably includes, unless otherwise defined, a mono- or bicyclic heteroaromatic ring system comprising up to four, preferably 1 or 2, heteroatoms each selected from oxygen, nitrogen and sulphur. Each ring may have from 4 to 7, preferably 5 or 6, ring atoms. A bicyclic heteroaromatic ring system may include a carbocyclic ring.

When substituted, a heteroaryl group may comprise up to three substituents. Preferably a substituent for a heteroaryl group is selected from the group hereinbefore defined as suitable aryl substituents.

Depending on the position of attachment of substituents, two or more diastereoisomers may be possible. In that situation the present invention includes the individual diastereoisomers and mixtures thereof.

The 2-hydroxy compounds of formula (4A) may be of the (2S) configuration or the (2R) configuration, or be provided as mixtures thereof. The (2S) configuration is preferred. The 2-hydroxy-substituted compounds of formula (5) are of the 2-(S) configuration.

When used herein, the term "pleuromutilins" includes pleuromutilin (compound of formula (1) as defined above) and pleuromutilin-related compounds such as, for example, pleuromutilin esters such as pleuromutilin 22-acetate or esters of fatty acids, mutilin, or mutilin 14-acetate. In particular, the term "pleuromutilins" includes pleuromutilin and mutilin 14-acetate, especially pleuromutilin.

When used herein, the term "pleuromutilins derivative" includes semi-synthetic derivatives prepared from the pleuromutilins produced according to the process of the present invention by, for example, functional group interconversion.

The pleuromutilins produced by the method of the present invention may be analyzed by HPLC. Pleuromutilins in broth and extraction samples can be determined using a C18 Waters Spherisorb S5 ODS2 column, 4.6×250 mm, with a 10 mm guard column. UV detection is at 205 nm. An isocratic mobile phase of 1 ml/min 45% MeCN in water and a 20 µl injection volume are used. For broth samples, 2 ml of whole broth is sonicated for 15 min with 4 ml of acetonitrile and filtered through a glass fibre filter paper prior to assay.

All publications, including but not limited to patents and patent applications, cited in this specification are herein incorporated by reference as if each individual publication were specifically and individually indicated to be incorporated by reference herein as though fully set forth.

The invention is illustrated by the following Examples.

EXAMPLE 1

Isolation of Pleuromutilin Using Toluene Extraction 1,364 L of *Clitopilus passeckerianus* NRRL 3100 whole broth at 1,280 mg/L pleuromutilin (1,746 g) was adjusted to pH 7 using 20% sodium hydroxide and extracted with a half volume of toluene. The extraction and separation was carried out using a Westfalia SA-7-01 centrifuge and Westfalia TA-7 disc stack centrifuge. Pump flows were adjusted to give 3 L-min whole broth and 1.5 L/min toluene. 681 L of toluene extract at 2,573 mg/L (1,751 g pleuromutilin) was obtained. (100% Stage yield)

6.76 L of part concentrate toluene extract prepared from the pleuromutilin extract, containing 17.74 g/L pleuromutilin (119.9 g), was further concentrated to 760 ml (15.8% w/v pleuromutilin) (at 60° C., in vacuo). The toluene concentrate was allowed to cool to room temperature with stirring and crystallisation commenced. The slurry was left at 5° C. overnight. Crystals were recovered by filtration on Whatman number 541 paper, washed with 2×20 ml cold heptane and dried for 48 hr at 55° C., 900 mBarg. 89.6 g of 100% pure crystalline pleuromutilin were obtained. (75% stage yield)

EXAMPLE 2

Isolation of Pleuromutilin Using Toluene Extraction 2,600 L of *Clitopilus passereckianus* NRRL 3100 fermentation broth, containing pleuromutilin at 1500 ug/g, were extracted with toluene at a broth/solvent ratio of 2:1 using a Westfalia CA226 scroll decanter. The pH was maintained between 6.8-7.5 (1M NaOH), and the extraction carried out at ambient temperature. Passage through a Westfalia TA-7 separator was used to polish the rich solvent stream. 1,275 L of rich solvent, containing 2400 ug/ml of pleuromutilin were collected. (Solvent extraction yield 76%)

1,275 L of pleuromutilin rich toluene were concentrated to 22.5 L (16% w/w) using vacuum distillation, 60-75° C. and 25 in Hg. (Concentration yield 93.5%)

The 22.5 L of pleuromutilin concentrate was divided into two approximately equal aliquots and further concentrated on a rotary evaporator (70° C.) to between 40-50% w/w (crystallisation observed from approximately 25% w/w). Crystallisation was completed overnight in an ice/water bath.

The product was recovered via filtration through a No. 54 Whatman filter paper. The weighed, wet product (2×1.83 kg) was slurried in 1 L of toluene per kg of wet product for 2 min and the product again recovered via filtration. The dry bed was washed with 0.5 kg toluene per kg of original wet product. (Crystallisation yield 86.7%)

2×1.5 kg wet product dried overnight at 45-50° C., under vacuum to give a total of 2.59 kg of pleuromutilin product at 95.7% purity. (Overall yield 61.5%)

EXAMPLE 3

Isolation of Pleuromutilin Using MIBK Extraction 1,397 L of *Clitopilus passeckerianus* NRRL 3100 whole broth containing 1,280 mg/L pleuromutilin (1,788 g) was adjusted to pH 7 using 20% sodium hydroxide. The whole broth was extracted with a half volume of MIBK. The extraction and separation was carried out using a Westfalia SA-7-01 centrifuge and Westfalia TA-7 disc stack centrifuge. Pump flows were adjusted to give 3 U-min whole broth, and 1.5 L/min MIBK. 628 L of MIBK extract at 3,010 mg/L was obtained (1,890 g pleuromutilin). (100% Stage yield)

2.82 L of part concentrated MIBK extract, prepared from the pleuromutilin extract, containing 39.02 g/L pleuromutilin (110 g) was further concentrated to 0.275 L (40% w/v pleuromutilin). The concentrate was cooled to 27° C. and crystallisation commenced. An equal volume of heptane was added dropwise over 20 min with vigorous agitation. The slurry was held at ambient temperature for 1 hr and then at 5° C. overnight. Crystals were recovered by filtration on Whatman number 541 paper washed with 2×20 ml cold heptane and dried for 48 hr at 55° C., 900 mBarg. 98.6 g of 96% pure crystalline pleuromutilin were obtained. (86.1% Stage recovery)

EXAMPLE 4

Isolation of Pleuromutilin Using MIBK Extraction

A 4500 L fermentation of *Clitopilus passeckerianus* NRRL 3100 containing 4.08 kg of pleuromutilin was extracted with half volume MIBK. The extraction and separation was carried out using a Westfalia CA226 counter current decanter, and Westfalia TA-7 disc stack centrifuge. Phases were pre-mixed using a Sulzer static mixer. Maintaining a 2:1 ratio of broth to MIBK, flow rates were increased throughout the process from 3 and 1.5 L/min, to 7 and 3.5 L/min. No degradation of phase separation or extraction efficiency was observed at these flows. MIBK extract was concentrated in vacuo to approximately 10% w/v pleuromutilin. 3.62 kg of pleuromutilin were recovered to rich extract. (Stage yield 89%)

1 L of partially concentrated MIBK extract, from Example 3, containing approximately 100 g of pleuromutilin, was further concentrated to 35% w/v pleuromutilin (at 60° C., in vacuo.). The concentrate was transferred to a 3 L flask and stirred at 250 rpm. The concentrate was allowed to cool to room temperature and approximately 30 mg of seed crystals were added. Crystallisation was observed after about 30 min.

1.1 volumes of heptane were then added at 10 ml/min, monitoring the stirrer rate to ensure good mixing without excessive splashing. After 1.5 hr at room temperature, the vessel was transferred to a 5° C. room for 2 hr. Crystals were recovered on a Whatman 541 paper by vacuum filtration. The crystal cake was washed with 2×10 ml of heptane, and dried at 50° C., 900 mbar for 48 hr. 84 g of 94% pure pleuromutilin crystals were obtained. (Stage yield 79%)

EXAMPLE 5

Decolourisation of Pleuromutilins from an MIBK Extract Using Activated Carbon Treatment 13 kg of MIBK semi-concentrate containing approximately 20% w/w pleuromutilins was treated with 173 g Norit GSX powdered carbon [Norit UK Ltd, Clydesmill Place, G32 8RF, UK] and stirred for 5 minutes. The carbon treated concentrate was filtered through a Celite bed [Harborlite UK Ltd, Livingstone Rd, HU13 OEG, UK] to remove the carbon.

Colour based on measurement of Yellowness Index (as defined in standards for measurement of optically clear solutions ASTM D 5386-93b and EN1557), reduced from 32.3 to 18.2 (47% removal).

12 kg of the carbon treated rich concentrate was reduced to 6 kg using rotary evaporation and transferred to a 30 L glass reactor, previously warmed to 50° C. using a hot water coil and 8 L of warmed MIBK. The MIBK was drained immediately prior to concentrate transfer.

The hot water to the coil was closed and 7 L of heptane was added to the concentrate, with agitation, over 25 min. The initial temperature during heptane addition was between 55-35° C., followed by natural cooling. On completion of the heptane addition, glycol was introduced to the coil and the temperature reduced to 4° C. for crystallisation. The mixture was stirred for 60 min.

The crystals were recovered via Buchner filtration and the cake washed with 2 L of heptane at room temperature. The product was dried overnight on stainless steel trays under vacuum at ambient temperature to yield pale cream free flowing granular crystals (97.7% pleuromutilins). (Stage yield 88.3%)

EXAMPLE 6

Reduction of Mutilin Impurities by Ethyl Acetate Recrystallisation 12 g of crystals of pleuromutilins were dissolved in 100 ml of ethyl acetate. The solution was concentrated to 20% w/w and transferred to a 50 ml round bottom flask contained in a water bath at 50° C. The water bath temperature was reduced to 20° C. and 45 ml heptane added with stirring over 30 min. The crystals were then stirred in an ice bath for 60 min. The recrystallised product was recovered via filtration and the cake washed with 10 ml heptane at ambient temperature. The product was dried overnight at ambient temperature under vacuum to yield white, fine, crystals containing 86.2% pleuromutilin and 2.9% mutilin 14-acetate reduction in mutilin 14-acetate was 77.0%. (Stage yield 82.1%)

EXAMPLE 7

Reduction of Mutilin Impurities by MIBK Recrystallisation 30 g of Pleuromutilins containing mutilin 14-acetate were dissolved in 80 ml MIBK with stirring, in a glass jacketed reaction vessel controlled at 60° C. The vessel was closed to atmosphere during dissolution. When the solid was fully dissolved, 80 ml of heptane at ambient temperature was added from a dropping funnel over 15-20 min whilst maintaining the temperature of the pleuromutilin solution at 60° C. On completion of the heptane addition the slurry was transferred to a 600 ml glass beaker, covered with cling film and stirred in a ice bath for 3 hr. The recrystallised product was recovered via vacuum filtration through a No. 54 Whatman filter paper and the cake washed in situ with 40 ml of a 3:1 heptane/MIBK mix. The cake was pulled dry on the filter paper using vacuum before being placed on a tray and dried overnight in a room temperature oven under vacuum with a slight air bleed. This process yielded 22.3 g of a white crystalline product containing 1.5% mutilin 14-acetate w/w (74.5% weight yield, 81.2% yield as pleuromutilin, 84% 14-mutilin acetate removal).

The invention claimed is:

1. A method for preparing one or more crystallised pleuromutilins comprising the steps of:
    a) culturing a pleuromutilins-producing microorganism in a liquid culture medium;
    b) extracting pleuromutilins from the unfiltered culture medium with a water immiscible organic solvent which is 4-methyl-2-pentanone (MIBK);
    c) concentrating the extracted pleuromutilins;
    d) directly crystallizing the pleuromutilins from MIBK using a miscible non polar solvent which is heptane.

2. The method according to claim 1, wherein the extracted pleuromutilins of step b or the concentrated pleuromutilins of step c are decolorised using activated carbon.

3. The method according to claim 1, for preparing pleuromutilin:

4. The method according to claim 1 wherein the pleuromutilins- producing microorganism is a *Clitopilus* species, an *Octojuga* species, a *Gerronema* species, or a *Psathyrella* species.

5. The method according to claim 1 wherein the extraction is conducted at about 10° C to about 50° C.

6. The method according to claim 1 wherein the pH of the liquid culture medium prior to extraction is in the range pH 6 to 8.

7. The method according to claim 1 wherein a ratio of 4:1 to 1:4 equivalent volume of MIBK to unfiltered culture medium is used for the extraction.

8. The method according to claim 1 wherein the pleuromutilins in step c are concentrated in MIBK to a concentration of 20% to 45% w/w.

9. The method according to claim 8 wherein the pleuromutilins in step c are concentrated in MIBK to a concentration of 35% to 40% w/w.

10. The method according to claim 1 wherein the initial temperature of the MIBK containing solution used for recrystallisation in step d is from 45° C. to 60° C., followed by cooling to from 25° C. to 35° C.

11. The method according to claim 10, wherein the initial temperature is from 50° C. to 55° C., followed by cooling to approximately 30° C.

12. The method according to claim 1 wherein 1 to 1.5 volumes of heptane is added in step d.

13. The method according to claim 1 wherein the crystallised pleuromutilins which are the product of step d are further purified by recrystallisation.

14. The method according to claim 13 wherein mutilin 14-acetate is selectively removed from the crystallised pleuromutilins by recrystallisation from ethyl acetate and heptane.

15. The method according to claim 14 wherein the concentration of pleuromutilins in ethyl acetate and heptane as recrystallisation solvent is from 20% to 40% w/w.

16. The method according to claim 10, wherein the initial temperature is from 45° C. to 50° C., followed by cooling to from 15° C. to 25° C.

17. The method according to claim 16 wherein the MIBK and heptane mixture of step d is cooled to 0° C. to 5° C. after heptane addition.

18. The method according to claim 13 wherein mutilin 14-acetate is selectively removed from the crystallised pleuromutilins by recrystallisation from MIBK and heptane.

19. The method according to claim 18 wherein the concentration of pleuromutilins in MIBK and heptane as recrystallisation solvent is from 20% to 45% w/w.

* * * * *

UNITED STATES PATENT AND TRADEMARK OFFICE
CERTIFICATE OF CORRECTION

| | | |
|---|---|---|
| PATENT NO. | : 7,556,948 B2 | Page 1 of 1 |
| APPLICATION NO. | : 10/524099 | |
| DATED | : July 7, 2009 | |
| INVENTOR(S) | : Michael John Rees et al. | |

It is certified that error appears in the above-identified patent and that said Letters Patent is hereby corrected as shown below:

On page 1, (75) Inventors, should be:
Keith Graham Robins, Anna Louisa Stefanska, Jan Edward Thirkettle, Michael Sidney Verrall, David Alan Yeandle Signed and Sealed this Eighteenth Day of August, 2009

David J. Kappos
*Director of the United States Patent and Trademark Office*